United States Patent [19]

Semenov et al.

[11] Patent Number: 4,653,001

[45] Date of Patent: Mar. 24, 1987

[54] DEVICE FOR PROCESSING ELECTRO-OCULOGRAPHIC SIGNALS

[75] Inventors: Pavel A. Semenov; Svyatoslav N. Fedorov; Emilia M. Mironova; Eleonora V. Egorova, all of Moscow, U.S.S.R.

[73] Assignee: Moskovsky Nauchnoissledovatelsky Institute Mikrokhirurgii Glaza, Moscow, U.S.S.R.

[21] Appl. No.: 716,860

[22] Filed: Mar. 28, 1985

[30] Foreign Application Priority Data

Apr. 2, 1984 [SU] U.S.S.R. .............................. 3718818

[51] Int. Cl.$^4$ .................. G06F 15/42; G06G 7/60
[52] U.S. Cl. .................................. 364/415; 128/745
[58] Field of Search ................. 364/415; 128/745, 774

Primary Examiner—Jerry Smith
Assistant Examiner—Kimthanh Bui
Attorney, Agent, or Firm—Lilling & Greenspan

[57] ABSTRACT

A device for processing electro-oculographic signals comprises series-connected a sensor of an EOG signal, an amplifier-multiplexer, a low-pass filter, a high-pass filter, an analog-to-digital converter, a stationary disturbance detection unit, a stationary disturbance suppressing unit, a multiplier, an adder-accumulator, a digital comparator, a time gate, a memory unit, a digital discriminator, and a control unit. In addition, the device comprises a stimulation period determination unit, an extrema determination unit, a first function generator, a second function generator, a classification unit, a visual stimulator, a calibrator, and a data display unit. The control unit has a plurality of outputs connected to respective additional inputs of the aforesaid units.

1 Claim, 12 Drawing Figures

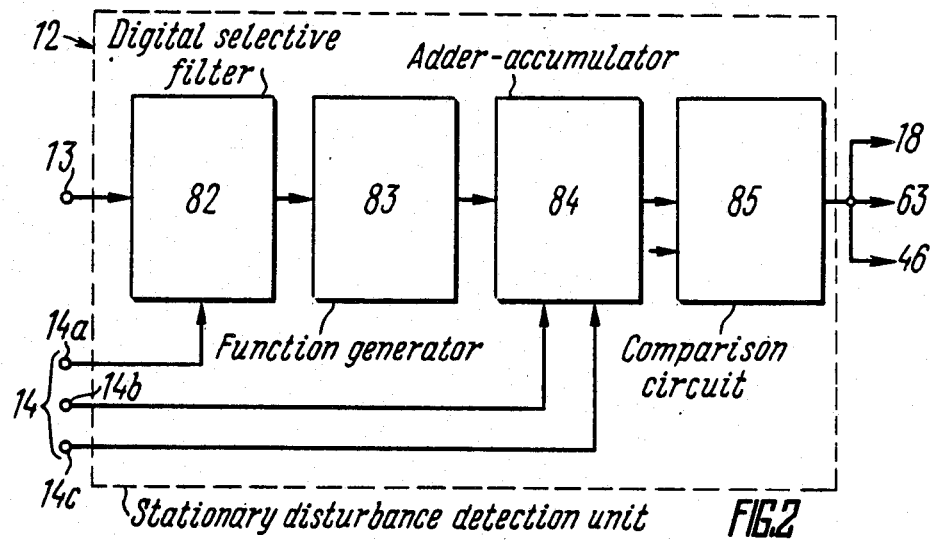

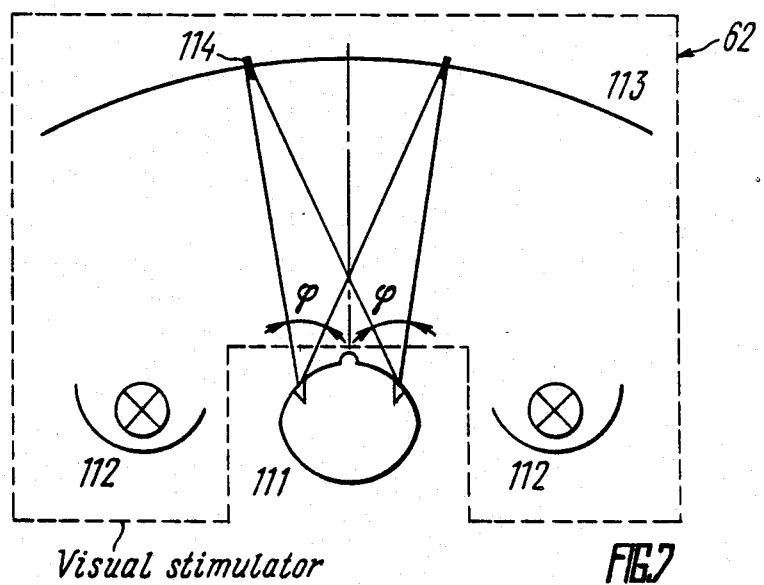
*Visual stimulator* FIG.7
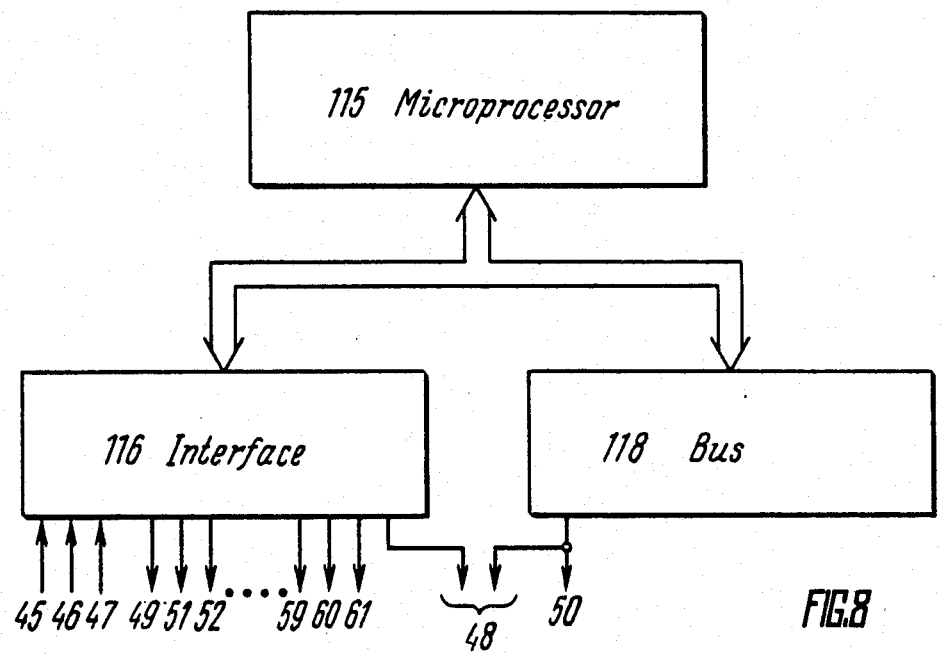
FIG.8

DEVICE FOR PROCESSING ELECTRO-OCULOGRAPHIC SIGNALS

TECHNICAL FIELD

The present invention relates to medical instrument-making practice and has particular reference to devices for processing electro-oculographic (EOG) signals and can find application in ophthalmological practice for carrying out electro-oculographic examinations with diagnostic purposes.

DESCRIPTION OF TECHNICAL PROBLEM

Processing of electro-oculographic signals implies in this particular case a sequence of handling operations on an electro-oculographic signal (i.e., amplification, filtration, integral transformations, discrimination of characteristic components of measurement signals), which are to be carried out in order to isolate (and measure) the amplitude of the intelligence component of an EOG signal from a mixture with a false EOG signal and a stationary disturbance, the intelligence component of an EOG signal resulting from eyeball rotation to a strictly metered preset angle of stimulation, a false EOG signal being caused by an occasional turning of the patient's head, and a stationary interference stemming from a poor contact of an EOG signal sensor with the patient's skin.

PRIOR ART

Known in the art are devices for processing electrooculographic signals (cf.: Cadwell 5200. Archives of Ophthalmology, 1983, vol. 101, No. 3, p. 345; Cadwell 7400. Archives of Ophthalmology, 1983, vol. 101, No. 4, p. 549; polygraph system planning manual. Nikon Kohden, Tokyo, Japan; Model 7310/7102/7402 Operating Manual. Life-Tech. Instruments, Houston, Tex.), featuring various serice capabilities, which incorporate an EOG signal sensor, an input amplifier-multiplexer, filters, an analog-to-digital converter, a data display unit, a visual stimulator, and a monitor unit.

However, the aforementioned devices fail to provide automatic yielding of the measurement and processing results, which involves visual "sorting" of a signal by the operator and hence leads to loss of operator's time and a necessity of his permanent watching for the coursing of a patient's examination. In addition, application of such devices necessitates repeated measurements with reset EOG signal sensors, or carrying out visual-and-manual filtration of a signal in the case of a heavy stationary disturbance which results in waste of time and adversely affected accuracy, respectively.

One more prior-art device for processing electrooculographic signals is known to use heretofore (cf. Pantops 500 Mode d'Emploi. Schlumberger Instruments et Systèmes), comprising an EOG signal sensor, an input amplifier-multiplexer, a low-pass filter, a high-pass filter, an analog-to-digital converter, and a data display unit, all the aforestated units being series-interconnected, as well as a calibrator, a visual stimulator, and a monitor unit adapted to synchronize the operation of the entire device.

However, said device suffers from the following disadvantages:

low accuracy of automatically yielded results since no reliable automatic extraction of true amplitudes of a desired EOG signal from a whole signal recorded is provided, nor a possibility of a visual monitoring by the operator and his control action upon the coursing of the recording process is ensured;

heavy distortions of the results obtained due to stationary disturbances.

In addition, no correct and confident results can be obtained with said device unless absolute synchronism of stimulation and patient's gaze shifting is provided.

The present invention is aimed at the provision of a device for processing electro-oculographic signals, having such a circuitry that would be capable of automatic yielding of high accuracy and reliability results of electro-oculographic measurements even under upset synchronism of stimulation and patient's gaze shifting, as well as in the presence of a stationary disturbance.

SUMMARY OF THE INVENTION

It is an object of the present invention to provide higher accuracy of processing electro-oculographic signals and yielding reliable measurement results under upset synchronism of stimulation and patient's gaze shifting.

It is another object of the present invention to provide greater immunity of signals obtained to stationary disturbances.

SOLUTION OF THE TECHNICAL PROBLEM AND EXEMPLARY EMBODIMENTS

The essence of the present invention resides in that a device for processing electro-oculographic signals, comprising an EOG signal sensor, an amplifier-multiplexer, a low-pass filter, a high-pass filter and an analog-to-digital converter, all said units interconnected in series, as well as a visual stimulator, a calibrator whose output is connected to a second input of the amplifier-multiplexer, and a data display unit, according to the invention, is also provided with series-connected a stationary disturbance detection unit, a stationary disturbance suppressing unit, a multiplier, an adder-accumulator, a double-output digital comparator, a time gate, a memory unit, a double-output digital discriminator, and a control unit, as well as a stimulation time determination unit whose output is connected to a second input of the time gate, a triple-output extrema determination unit, one of the outputs of said unit being connected to a second input of the stationary disturbance suppressing unit and to a second input of the control unit, while a second output of the extrema determination unit is connected to a second output of a first function generator, while said control unit has a number of outputs which are connected to additional inputs of respectively the calibrator, the amplifier-multiplexer, the analog-to-digital converter, the stationary disturbance detection unit, the stationary disturbance suppression unit, the stimulation time determination unit, the extrema determination unit, the second function generator, the adder-accumulator, the digital comparator, the time gate, the memory unit, the data display unit and the visual stimulator; besides, the output of the analog-to-digital converter is connected to the input of the stationary disturbance detection unit and to the second input of the stationary disturbance suppression unit, the second output of the digital comparator is connected to the second input of the extrema determination unit, the output of the stationary disturbance detection unit is connected to the second input of the data display unit and to the third input of the control unit, and the second output of the digital discriminator is connected to the third input of the data display unit.

The device for processing electro-oculographic signals, according to the present invention, enables one to considerably enhance the accuracy of automatically yielded data and provide their stability and immunity to a high-amplitude stationary disturbance and thereby to render the process of electro-oculographic measurements fully automated.

Practical application of the device proposed in the present invention makes it possible to reduce the amount of attending personnel eight times (one operator per eight devices) when carrying out population screening.

BRIEF DESCRIPTION OF THE DRAWINGS

In what follows the invention will now be disclosed in a detailed description of some specific illustrative embodiments thereof to be read with reference to the accompanying drawings. According to the invention, in the drawings:

FIG. 2 is a block diagram of the stationary disturbance detection unit;

FIG. 3 is a block diagram of the stationary disturbance suppression unit;

FIG. 7 is a schematic view of the visual stimulator;

FIG. 8 is a scaled-up view of the control unit;

DETAILED DESCRIPTION OF THE INVENTION

Figure 1:
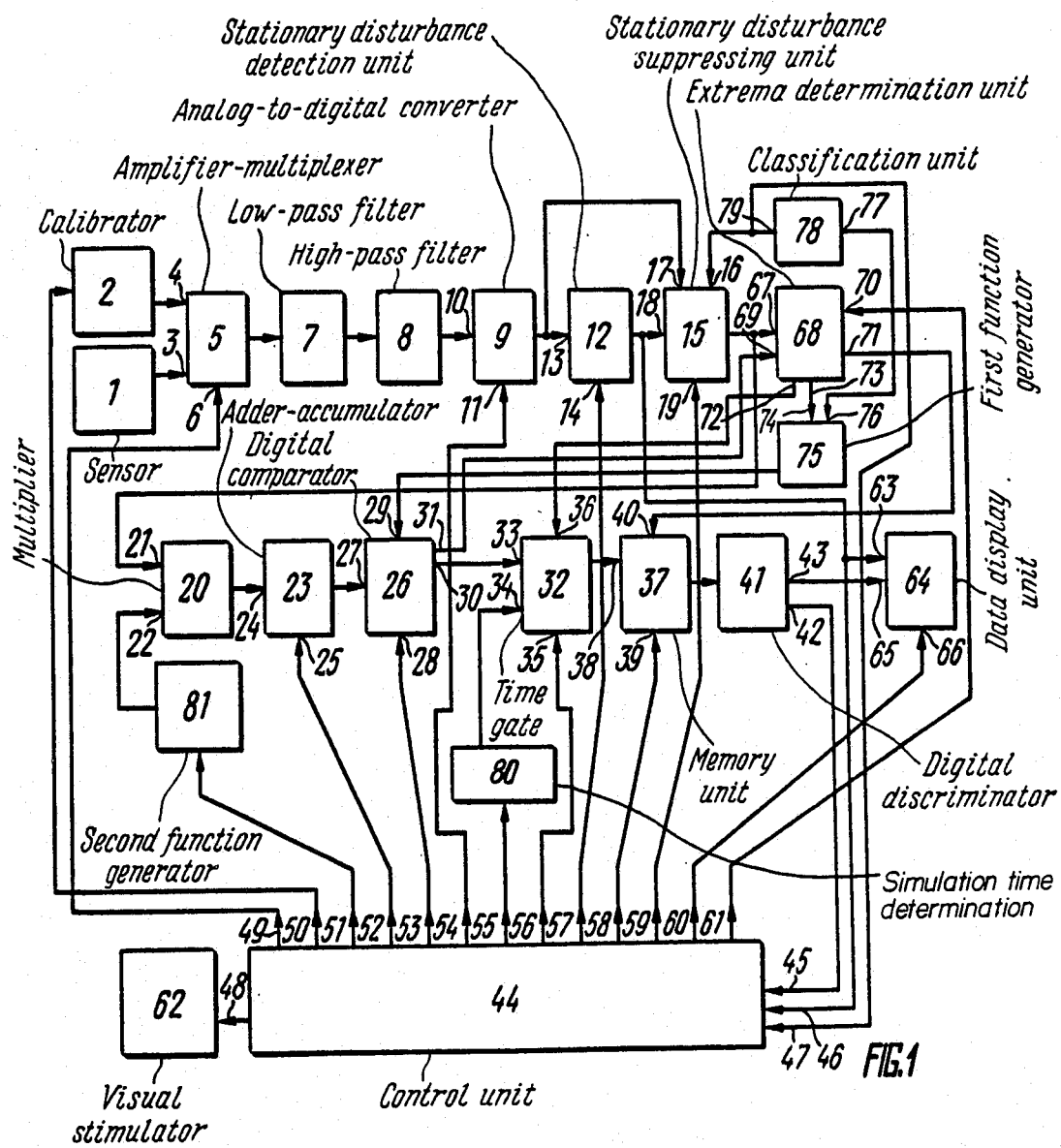
FIG. 1 is a block diagram of a device for processing electro-oculographic signals.

The device for processing electro-oculographic signals comprises a sensor 1 and a calibrator 2, both of them connected to a respective signal inputs 3, 4 of a triple-input amplifier-multiplexer 5 which has also a third input 6.

Connected to the output of the amplifier-multiplexer 5 are series-connected a low-pass filter 7, a high-pass filter 8, and a double-input analog-to-digital converter 9 having inputs 10 and 11. Connected to the output of the analog-to-digital converter 9 are series-connected a stationary disturbance detection unit 12 having two inputs 13 and 14, a stationary disturbance suppression unit 15 having four inputs 16, 17, 18, 19, a multiplier 20 having two inputs 21 and 22, an adder-accumulator 23 having two inputs 24, 25, a digital comparator 26 having three inputs 27, 28, 29 and two outputs 30, 31, a time gate 32 having four inputs 33, 34, 35, 36, a memory unit 37 having three inputs 38, 39, 40, a digital discriminator 41 having two outputs 42, 43, a control unit 44 having three inputs 45, 46, 47 and fourteen outputs 48, 49, 50, 51, 52, 53, 54, 55, 56, 57, 58, 59, 60, 61, as well as the visual stimulator 62. The output of the stationary disturbance detection unit 12 is connected also to the input 46 of the control unit 44 and to an input 63 of a data display unit 64 which has two additional inputs 65 and 66, the output 43 of the digital discriminator 41 being connected to said input 65. Connected to the output of the stationary disturbance suppression unit 15 is also an input 67 of an extrema determination unit 68 which has also inputs 69, 70 and three outputs 71, 72, 73, of which the output 71 is connected to the input 40 of the memory unit 37, the output 72 is connected to the input 36 of the time gate 32, and the output 73 is connected to an input 74 of a first function generator 75. The output of the first function generator 75 is connected to the input 29 of the digital comparator 26 and a second input 76 thereof is connected to an output 77 of a classification unit 78 which has also a second output 79 connected to the input 16 of the stationary disturbance suppression unit 15 and to the input 47 of the control unit 44. The output of the analog-to-digital converter 9 is connected also to the input 17 of the stationary disturbance suppression unit 15, and the output 31 of the digital comparator 26 is connected to the input 69 of the extrema determination unit 68.

In addition, the device under consideration comprises a stimulation time determination unit 80 whose input is connected to the output 55 of the control unit 44 and its output is connected to the input 34 of the time gate 32, a second function generator 81 which is controlled by signals delivered from the output 51 of the control unit 44, the output of the function generator 81 being connected to the input 22 of the multiplier 20.

The operation of the entire device is controlled by the control unit 44 which is connected as follows: the output 49 of said unit is connected to the input 6 of the amplifier-multiplexer 5, the output 50 is connected to the input of the calibrator 2, the output 52 is connected to the input of the adder-accumulator 23, the output 53 is connected to the input 28 of the digital comparator 26, the output 54 is connected to input 11 of the analog-to-digital converter 9, the output 56 is connected to the input 35 of the time gate 32, the output 57 is connected to the input 14 of the stationary disturbance detection unit 12, the output 58 is connected to the input 39 of the memory unit 37, the output 59 is connected to the input 19 of the stationary disturbance suppression unit 15, the output 60 is connected to the input 66 of the data display unit 64, and the output 61 is connected to the input 70 of the extrema determination unit 68.

Given below is a more detailed consideration of specific embodiments of the circuitry in a number of units of the device disclosed therein.

The EOG signal sensor 1 is in effect composed of two contact lamels coated with an Ag—AgCl compound and connected to the differential measuring input 3 of the amplifier-multiplexer 5. The lamels are placed at the internal and external canthi of a patient's eye.

The calibrator 2 is composed of a trigger flip-flop and an analog switch. The trigger flip-flop, e.g., of the JK-type (J=K="1") is switched over by a signal delivered from the output 50 of the control unit 44 and effects control over the analog switch which either connects the input of the amplifier-multiplexer 5 either to a reference calibration voltage or applies earth to it. The calibrator 2 is aimed at attaining higher stability of the results of measurement of an EOG signal. The process of processing a calibration signal is quite the same as the processing of a signal picked off from the sensor 1 provided that a logic signal "5=calibrator" is applied to the input 6.

The amplifier-multiplexer 5 is adapted for matching the level of signal picked up by the sensor 1 with the range of the conversion voltage of the analog-to-digital converter 9. The amplifier 5 is in fact a differential amplifier with an input analog multiplexer which applies the calibration voltage to the input 4 and an input EOG signal, to the input 3. The multiplexer is controlled by the logic signal "5=calibrator" delivered from the output 49 of the control unit 44 and applied to the input 6 of the amplifier-multiplexer 5, the logic level "1" of said signal corresponding to the connection of the calibrator 2, and the level "0", to the connection of the sensor 1.

The low-pass filter 7, usually either the RC or the LC type, is to limit the upper frequency of the signal.

The high-pass filter 8 which is in effect a differentiating circuit in this particular case, makes it possible to discriminate instrumentally the leading wavefronts of an input signal, corresponding to the instants when gaze shifts occur. Besides, the same circuit prevents the d.c. component of the signal from getting at the input of the analog-to-digital unit 9, said d.c. component resulting from infralow frequency drift of the bias voltage of the amplifier-multiplexer 5 and of the low-pass filter 7.

The analog-to-digital converter (ADC) 9 is to convert an analog signal into a digital code and may be based on, e.g., the digit-to-digit balancing technique. The ADC is triggered by the "9-start" signals delivered from the control unit 44 and applied to the input 11 of the ADC.

The stationary disturbance detection unit 12 isolates such a disturbance and compares its root-mean-square amplitude $\overline{a^2}$, or a similar value, e.g., $|\overline{a}|$ with a preset threshold value with the purpose of establishing the fact of a disturbance. A given stationary disturbance may be due to poorly applied electrodes, poor contact of the electrodes to patient's skin, or due to stray pick-up in the wires interconnecting the sensor 1 and the input of the amplifier-multiplexer 5. Thus, such a disturbance should be isolated and suppressed. As a rule, any disturbance features a narrow frequency band, its frequency being equal to that of power mains.

An embodiment of the block diagram of the stationary disturbance detection unit 12 is represented in FIG. 2. The unit comprises series-connected a digital selective filter 82, a function generator 83 (e.g., a squarer $x^2$, or determinant of an absolute value of $|x|$), an adder-accumulator 84 and a code comparator circuit 85. The digital selective filter 82 operates at a quantization frequency in response to a signal arriving at the input 14a from the control unit 44, and is tuned to the power mains frequency. Once the output data of the digital filter 82 have been converted in the function generator 83 under the laws of, e.g., $x^2$ or $|x|$, the sum of the converted values is accumulated in the adder 84 against a signal delivered from the control unit 44 at a quantization frequency, and applied to the input 14b. The adder 84 is reset to the initial state (before accumulation) in response to a signal arriving at the input 14c from the control unit 44, whereas accumulation occurs within a time interval set by the control unit 44. The value of the sum is then compared in the code comparator circuit 85 with a threshold value Z and, if the sum exceeds the threshold value, a logic signal is delivered to indicate the presence of a stationary disturbance, said signal being applied to the inputs 18, 63, 46 of the respective units. The threshold value Z is so selected as to isolate a disturbance having an amplitude above one quantum as read on the scale of the analog-to-digital converter 9 (FIG. 1).

The stationary disturbance suppression unit 15 (FIGS. 1, 3) is to suppress a disturbance until its intensity is reduced to a value comparable with the value of the less significant digit of the analog-to-digital converter 9 whenever said disturbance has been detected and the classification unit 78 permits its suppression. The stationary disturbance suppression unit 15 comprises a digital rejection filter 86 whose input and output are connected to the inputs of a digital commutator 87, and a double-input AND gate 88, whose output is connected to the control input of the digital commutator 87. The filter 86 is tuned to the power mains frequency.

The commutator 87 applies data to the data output of the unit 15 either from its input 17 or from the output of the digital rejection filter 86 (provided that the output 79 of the unit 78 equals "1") which operates at a quantization frequency in response to a signal delivered from the control unit 44 to the input 19.

The multiplier 20 performs digital multiplication of the data at the inputs 21 and 22.

The adder-accumulator 23 is for accumulating a sum of results from the multiplier 20, applied to the data input 24; it can incorporate, e.g., an adder and a gate register with reset. The adder 23 is controlled through its input 25 by the signals "23-accumulation" and "23-reset" delivered from the control unit 44, said signals carrying out respectively the gating of the sum accumulation and resetting the register of the adder-accumulator 23 into the initial state.

The second function generator 81 is for shaping a linearly increasing voltage symmetrical with respect to zero within constant-duration time intervals of a first type $$[t_1^{i-1}, t_1^i],$$

e.g., in the form of $$(2t - t_1^{i-1} - t_1^i),$$

or in a discrete form $$F_{81} = 2k - t_1^{i-1} - t_1^i; \qquad (1)$$

where $$k \, [t_1^{i-1}, t_1^i]$$

—the number of a time quantum;

$$t_1^{i-1}, t_1^i$$

—the numbers of time quanta respectively of the beginning and end of the i-th time interval of a first type.

Then the code (1) is utilized for determining an integral value of $I_i$:

$$I_i = \int_{t_1^{i-1}}^{t_1^i} (2t - t_1^i - t_1^{i+1}) U(t) dt, \qquad (2)$$

where U(t)—the input EOG signal, which is characteristic of an integral velocity of the EOG signal in the time interval $$[t_1^{i-1}, t_1^i],$$

which is of importance for finding the instant at which patient's gaze shifting occurs, i.e., when the said value reaches it maximum. Since the length of each time interval of the first type is constant and equals $$\Delta t = t_1^i - t_1^{i-1}, V_i,$$

so the code (1) is transformed to $$F_{81} = (2i - \Delta t)\epsilon[-\Delta t, \Delta t], \quad (3)$$

where i=0 to $\Delta t$—the number of a time quantum within the i-th running first-type time interval having a length of $\Delta t$, i.e., is in fact a step function symmetrical with respect to zero and having a step of 2. The function (2) can be formed by a binary counter with a step of $+2$ (counting pulses arriving at the second digit relative to the less significant digit) in response to the signal "81-1" delivered from the control unit 44. The signal "81-reset" is also delivered from the control unit 44 at the beginning of each first-type time interval for the initial counter setting.

The first function generator 75 is for forming the value of the functional threshold FT which defines the width of the dead zone of the digital comparator 26. The value of the FT is associated with the value of the code $|U|_{max}$ of the maximum of the module U(t) which is applied to the input 14 of the unit 75 from the output 73 of the extrema determination unit 68, via a nondecreasing functional relationship f(u), e.g., of the following types:

$$F_{81} = (2i - \Delta t)\epsilon[-\Delta t, \Delta t], \quad (3)$$

$$df/du = \text{const}, \ U\epsilon[U_{min}, U_{max}] \quad (4)$$

$$\lim_{u \to \infty} df/dU = 0 \quad (5)$$

$$\lim_{u \to \infty} df/dU = \infty \quad (6)$$

$$\left.\frac{d^2f}{dU^2}\right|U = U_{min} \cdot \left.\frac{d^2f}{dU^2}\right|U = U_{max} < 0 \quad (7)$$

The linear relation (4) implies equal level of saccadic and nystagmoid eye movements at different maximal levels of an input signal. This holds true for inconsiderable spread in values of $|U|_{max}$.

The relation (5) features the property of a maximum "saturation" with an increase in the argument. This holds good for going from a region of low signal values which corresponds to some retinopathies and a higher level of saccadic values, to a region of normal values. Among such relations are $\sim \ln(u-a), \sim \sqrt{u}$, and the like, where 'a' stands for a parameter.

The relation (6) corresponds to transition from a region of normal values of the electro-oculographic signals to a region of superhigh (supernormal) values, which is also indicative of the presence of some retinopathies when the level of saccadic eye movements rises.

The relation (7) features the best approximating properties and incorporates the relations (4), (5) and (6), which enables it to be applied for a widest variety of patients suffering from diverse retinopahties. There pertain to such relations $\sim \arcsin(u-a), \sim (u-a)^3$, and the like, where ('a') denotes a preset parameter.

The best results can be obtained for practical applications from utilization of the relation (5) or (7), as well as of piecewise-linear or step-by-step approximations of such relations. Coefficients and constant parameters of these relations are selected proceeding from optimum conditions of signal detection, in particular, from the Neumann-Pierson criterion and a degree of suppression of false local extrema on a rising signal wavefront. An increase in the value of FT (in case a signal "patient with poor vision" appears at the output 77 of the unit 78) makes it possible to reduce the probability of a "false alarm" in the Neumann-Pirson criterion and to "weaken" the conditions for detection of an EOG signal in patients with poor eye-sight.

Thus, used as the first function generator 75 may be a function digital code translator (e.g., a fixed memory), wherein the relation $FT(|U|_{max})$ is recorded. In this case the data inputs 74 and the input 76 of the unit 75 are in fact the address lines of the fixed memory, while the outputs of said fixed memory serve as the output of said unit.

Insertion of the functional threshold FT enables one to normalize, as it were, the value of $I_i$ (refer to Eqn.(2) to the value of FT and to manipulate solely relative values. The discrete form of the expression (2) is realized by the units 20, 23, 81, while the time interval $$[t_1^{i-1}, t_1^i]$$

is set by the control unit 44. True normalization of $I_i$ (see Eqn.(2) to FT is ineffective, since it will result in replacement of the unit 75 by a divider interposed between the units 23 and 26, which will deliberately feature more complicated realization than the unit 75. Nevertheless, such a version is also practicable.

Figure 4:
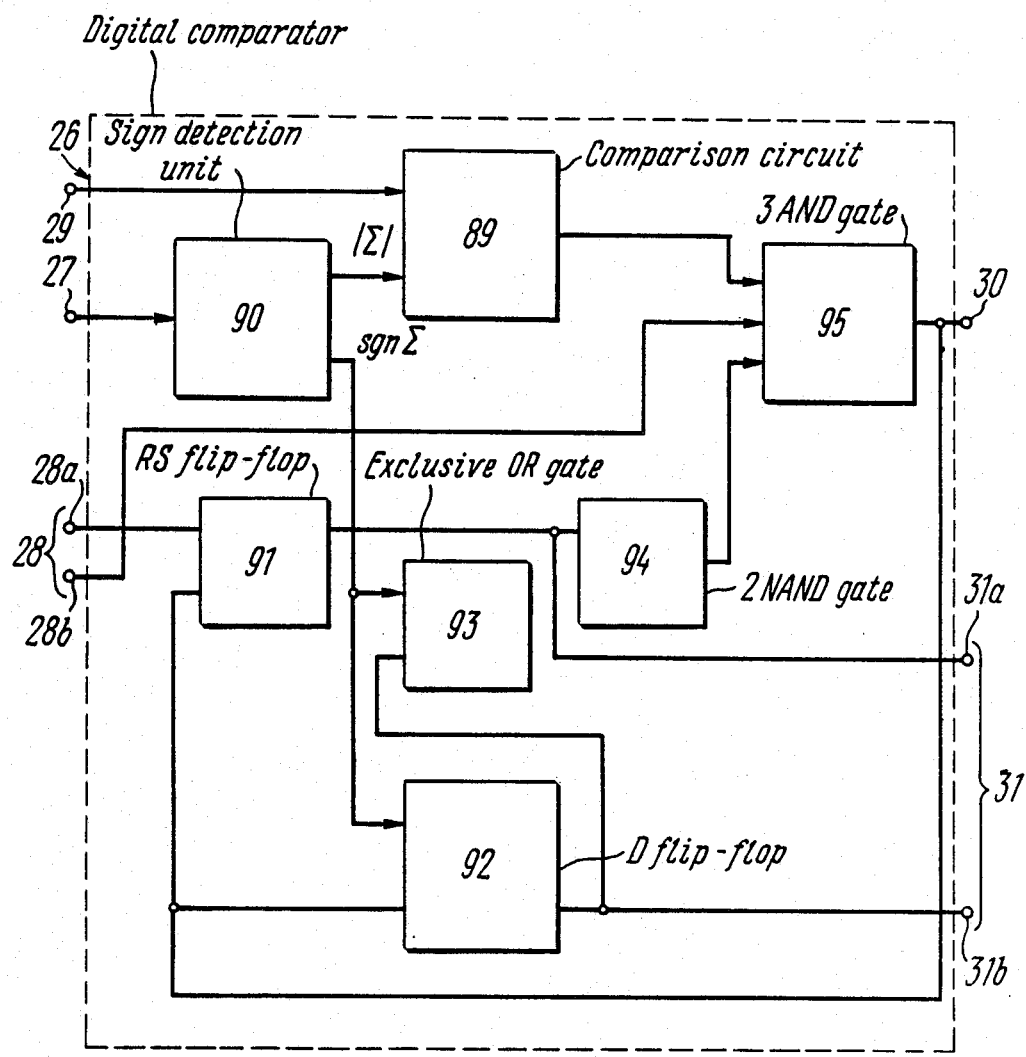
FIG. 4 is a block diagram of the digital comparator.

FIG. 4 exemplifies a block diagram of the digital comparator 26.

The digital comparator 26 comprises a code comparison circuit 89 one of whose inputs is the comparator input 29, while connected to the other input thereof is the output of a unit 90 for detection of the sign and sum modulus at the comparator input 27. The comparator incorporates also an RS sign blocking flip-flop 91 and connected to the other output of the sign detection unit 90 a preceding sum sign D-flip-flop 92 having an inverse output, and an exclusive OR gate 93 serving as a comparison circuit for the signs of the running sum and the preceding sum. A 2NAND gate 94 is connected, with its respective inputs, to the output of the RS flip-flop 91 and to the output of the exclusive OR gate, while a 3NAND gate 95 is connected, through its respective inputs, to the output of the comparison circuit 89, to the output of the 2NAND gate 94 and to the input 28b of the comparator.

The function of the digital comparator 26 is to isolate the first time instants $$T_2^i$$

forming the second-type time intervals $$[T_2^{i-1}, T_2^i],$$

when the code of FT from the unit 75 (first function generator) is less than the modulus of the sum $\Sigma$ in the adder-accumulator 23 provided that the sign of the sum at the time instant $T_2^i$ is opposite to the sign of the sum on a preceding time interval $[T_2^{i-1}, T_2^i]$.

When no preceding time interval has occurred (in case of triggering the device), one should search for such a value of $T_2^i$ that would satisfy the condition $|\Sigma| \geq FT$ at either sign of the sum. Otherwise speaking, the digital comparator 26 is essentially a serial alternating-sign detector featuring the width of a dead zone round "0" equal to 2FT. Upon initial triggering of the device the sign blocking flip-flop 91 is set to "0" by a signal "26-search wait" applied to the input 28a from the control unit 44 and blocks the passage of a signal from the circuit 93 of comparison of the signs of the running and preceding sums at the time instant $T_2^{i-1}$ at the output of the gate 94. The running sum sign $\Sigma$ is delivered from the output of the unit 90 to the input of the gate 93 and to the D-input of the flip-flop 92. The running sum modulus $|\Sigma|$ is applied from the output of unit 90 to the code comparison circuit 89, while applied to the second data input 29 of the circuit 89 are applied the FT data from the output of the first function generator 75. Once a time instant occurs satisfying the condition $|\Sigma| \geq FT$, the control unit 44 delivers the gating signal "26-permission to compare" to unset the sign-blocking flip-flop 91 and to set the preceding sum sign flip-flop 92 to the respective state. Then a narrow pulse is delivered to the gate 93 to indicate that a new time interval $[T_2^i, T_2^{i+1}]$ begins. The extrema determination unit 68 starts searching for an extremum (min/max) whose type would correspond to the logic level of a signal at the output 31b. Within the initial time interval (at the instant when the device is triggered) the unit 68 searches for extrema of two types at a time in accordance with a blocking signal "search for min/max" at the output 31a.

The stimulation time determination unit 80 is for determining the duration of a stimulation period (that is, the time interval between two consecutive changeovers of the visual stimuli of the unit 62) as a whole number of the quantization periods. The unit is in effect a binary counter whose data outputs are connected to the input 34 of the time gate 32. The counter counts up or resets against the respective signals "80-"1" and "80-reset" from the control unit 44. The unit 80 can be incorporated in the control unit 44 provided the stimulation period timer of the unit 44 is a digital one.

The patient classification unit 78 is in fact two selectors that shape two logic signals. A signal permitting suppression of a stationary disturbance is applied at the output 79 by the operator if a poor contact between the sensor 1 and patient's skin occurs, to allow the unit 15 to operate when the amplitude of a stationary disturbance exceeds a definite preset value. A signal "patient with poor eyesight" appears at the output 77 if the patient features poor gaze fixation, or the level of nystagmoid movements of patient's eye exceeds a preset permissible value. The signal is to correct the value of the functional threshold produced by the first function generator 75.

Figure 5:
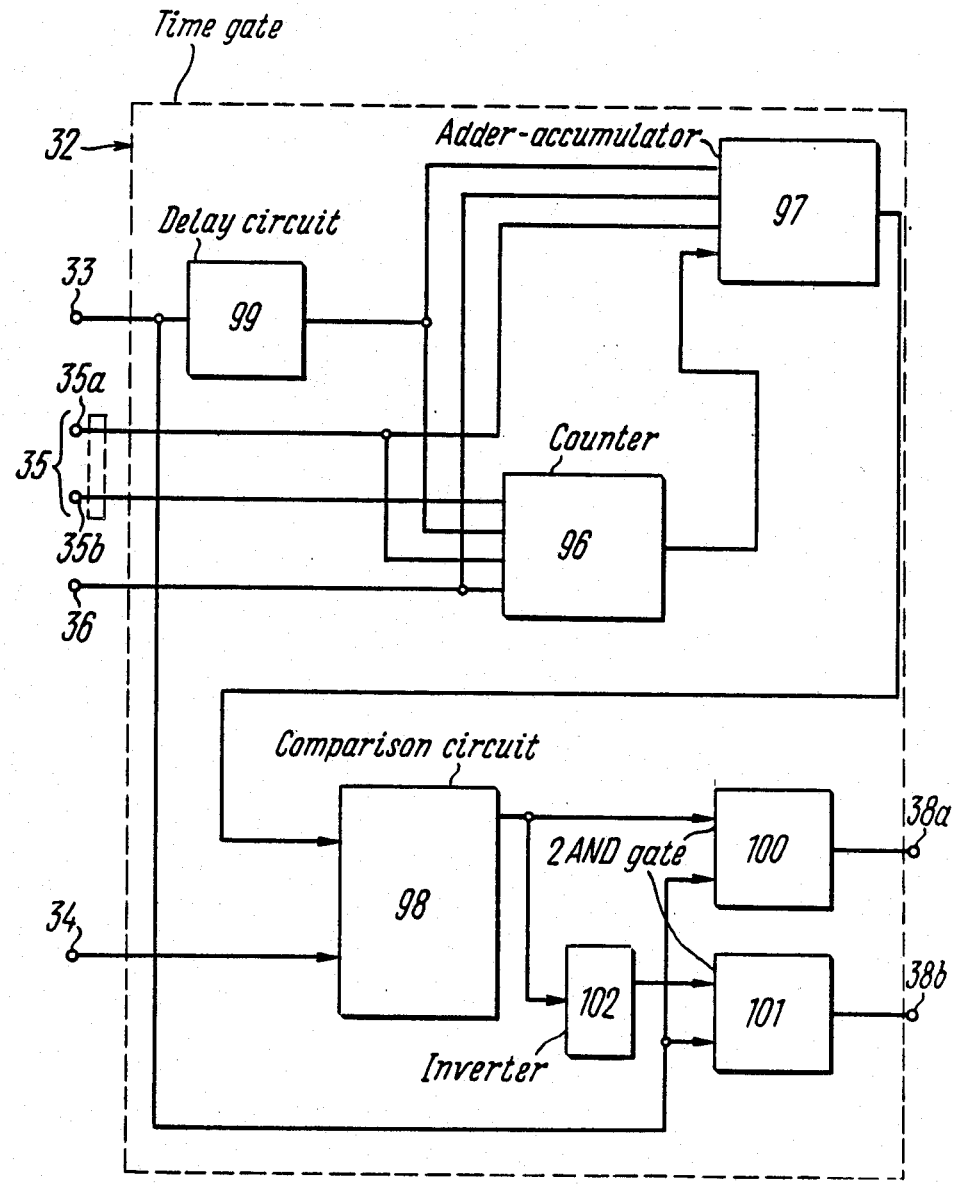
FIG. 5 is a block diagram of the time gate.

The time gate 32 whose schematic diagram is illustrated in FIG. 5, is for producing a signal "memory clear" of the unit 37 at the output 38b, and a signal (at the output 38a) "recording" in the memory unit 37 the extrema from the unit 68, the time interval $\Delta T$ between which satisfies the following relation:

$$\Delta T \epsilon [(1-\delta)T_s, (1+\delta)T_s] \quad (8)$$

where
$T_s$—stimulation period determined by the unit 80;
$\delta$—time interval width coefficient.

Whenever the time interval between any two extrema fails to satisfy the relation (8), a memory clear signal is produced at the output 38b.

The time gate 32 comprises a counter 96 having four inputs, of which three are the inputs 35a, 35b and 36 of the time gate 32, and series-connected to the counter 96 an adder-accumulator 97 and a code comparison circuit 98 whose second input is the input 34 of the time gate 32. In addition, the time gate comprises a delay circuit 99 whose output is connected to the second input of the adder-accumulator 97 and to the third input of the counter 96. The third input of the adder-accumulator 97 is connected to the input 36 of the time gate and the input of the delay circuit 99 is the input 33 of the time gate 32. Connected to the output of the code comparison circuit 98 is a logic circuit comprising two "2AND" gates 100, 101 having the common input 33 of the time gate, and an inverter 102, while the output of the code comparison circuit 98 is connected to the input of the inverter 102 and to the second input of "2AND" gate 100, and the second input of the "2AND" gate 101 is the output of the inverter 102. The outputs 38a and 38b are the outputs of the "2AND" gates 100 and 101, respectively. The fourth input of the adder-accumulator 97 is the input 35a of the time gate 32.

Upon triggering the device the contents of the counter 96 and the adder-accumulator 97 equal zero (a signal "32-reset" is applied to the input 35a). The counter 96 accumulates in response to a signal "32-+1" delivered from the output 56 of the control unit 44 and applied to the input 36b, at a quantization frequency until a signal telling of detection of a first local extremum, is delivered from the unit 68 to the input 36 to add the contents of the counter 96 to the contents of the adder-accumulator 97, records the sum again into the adder 97 and resets the counter 96.

On arrival of a signal at the input 33 from the digital comparator 26 at the instant when a next second-type time intervals terminates, the contents of $\Delta T$ in the adder-accumulator 97 are compared with the value of the stimulation period $T_s$ (at the input 34) in the code comparison circuit 98 in accordance with the condition (8). Depending on the result of the analysis of the condition (8), the gates 100, 101 and 102 shape either a signal "recording" at the output 38a or a signal "reset" at the output 38b, both of the signals being gated by a signal at the input 33.

A signal appearing at the input 33 after having passed through the delay circuit 99 (the delay value $\tau \geq$ the duration of a signal at the input 33), records the contents of the counter 96 into the adder-accumulator 97 and resets the counter 96. Now the adder-accumulator 97 contains data on the time interval between the extremum on the preceding second-type time interval and the last detected extremum on the running second-type time interval.

The coefficient $\delta$ in the expression (8) is determined by possible nonuniformity of bioelectric potential in gaze shifting to the right and left following the changing-over of the stimulating light-emitting diodes of the visual stimulator 62 and can assume any value within 0.05 for various patients.

The memory unit 37 is in fact a structure of memory registers of the FIFO (first-in, first-out, cf. J. Walkerley, Microcomputer architecture and firmware), which can be implemented on the base of, e.g., a set of series-interconnected shift registers having a digit capacity equal to the digit capacity of codes delivered from the unit 68 to the input 40. An input signal from the output 38a of the unit 32 (FIG. 5) is a common signal of recording synchronization and shifting of all registers, while signals from the output 38b and a signal "37-clear" delivered from the control unit 44 to the input 39 are the reset signals joined according to an OR circuit.

The memory unit 37 has data inputs from each of the registers, as well as a logic output, appearance of the level "1" at which corresponds to the memory unit 37 filled to capacity.

Figure 6:
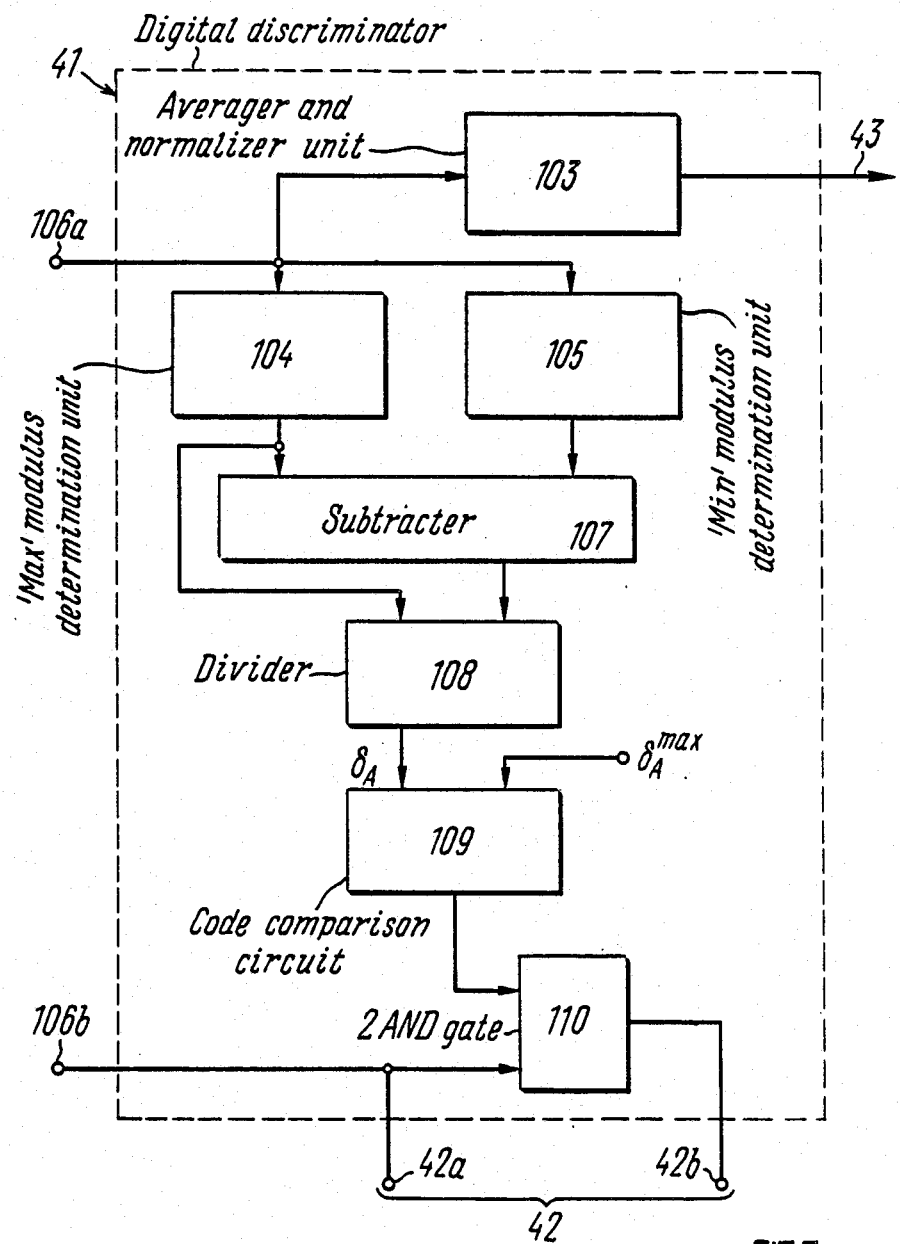
FIG. 6 is a block diagram of the digital discriminator.

An exemplary realization of the circuit of the digital discriminator 41 is represented in FIG. 6.

The digital discriminator 41 is for control over uniformity of the data recorded in the memory unit 37. The discriminator incorporates an averager and normalizer unit 103, a maximum absolute value determination unit 104, a minimum absolute value determination unit 105 having a common input 106a which is in fact the data output of the memory unit 37. In addition, the digital discriminator comprises a subtracter 107 connected, through its respective inputs, to the outputs of the units 105 and 104, a divider 108 whose dividend output is connected to the output of the subtracter 107 and the divisor output is connected to the output of the maximum absolute value determination unit 104, a code comparison circuit 109 connected to the output of the divider 108, and a double-input 2AND gate 110 whose one input is the output of the code comparison circuit 109 and the other input is the input 106b of the unit connected to the logic output of the memory unit 37, said output indicating that the memory unit 37 is filled to capacity. The input 106b serves also as the output 42a of the digital discriminator 41, while the output of the 2AND gate 110 is at the same time the output 42 of the discriminator 41. The output of the averager and normalizer unit 103 is the output 43 of the discriminator 41.

Checking for uniformity consists in comparison of the value of $\delta_A$:

$$\delta_A = \frac{\text{MAX}_{abs\ 37} - \text{MIN}_{abs\ 37}}{\text{MAX}_{abs\ 37}}, \quad (9)$$

where

MAX$_{abs\ 37}$—maximum value (as for modulus) of the contents of the unit 37;

MIN$_{abs\ 37}$—minimum value (as for modulus) of the contents of the unit 37, with the threshold value of $$\delta_A^{max}.$$

In case of filling the memory unit 37 to capacity (the level at inputs 106b equals "1") and $$\delta_A \leq \delta_A^{max},$$

an automatic search for an intelligence EOG signal terminates with the appearance of a signal having the logic level of "1" at the output 42b or otherwise, when $$\delta_A > \delta_A^{max},$$

there is delivered a combination signal "unequiangular fixation" (a combination of $(42a="1") \wedge (42b="0")$). The parameter $$\delta_A^{max}$$

is characteristic of nonuniformity of the signal extrema as recorded in the memory unit 37. Such nonuniformity may be due to asymmetrical (with respect to the optic axis) application of electrodes, or due to an unequiangular gaze fixation by the patient (which may be the case with strabismus). The permissible value of $$\delta_A^{max}$$

falls within the range of 0.1 and $$0.5\ (\delta_A^{max} \leq 0.5).$$

If a higher value of $\delta_A$ is noted, this points to pronounced pathologic changes in the oculomotor system, which is indicated by a signal "unequiangular fixation" delivered to the control unit 44.

Some other criteria may be employed for nonuniformity check, such as the ratio of a root-mean-square deviation to a mean value of the moduli of the data contained in the memory unit 37, the ratio of a difference (MAX−MIN) to a mean value or median, and so on.

The value of $$\delta_A^{max}$$

is applied to the code comparison circuit 109 which establishes the level "1" at the output when $$\delta_A \leq \delta_A^{max}.$$

The unit 103 determines a mean value of the modulus of the data recorded in the memory unit 37 at the data input 106a, normalizes said mean value to the stimulation angle $\phi$ (i.e., an angle between the light stimuli of the visual stimulator 62 with respect to patient's eye) to obtain a normalized constant electro-oculographic eye potential (cf. Arden G. B., Barrada A., Kelsey J. Brit. J. Ophthal.", 1962, 46, 8, p. 449 to 467) and withdraws the results to the data display unit 64 via the data output 43. Another statistical assessment may be used instead of a mean value of the modulus, e.g., the median of the moduli of amplitudes.

The visual stimulator 62 meets the standard requirements imposed by EOG examination; it is represented in FIG. 7, illustrating a patient 111, background illumination lamps with reflectors, a stimulation screen 113 and stimulation light-emitting diodes 114. The patient 111 is so spaced apart from the screen 113 that the stimulation angle $\phi$ equal to the angle of gaze shifting (for each eye) from one stimulation light-emitting diode 114 to the other be equal to a preset magnitude (as a rule, $\phi = 10°$ to $40°$ according to Arden's technique; cf. Arden G. B., Barrad A., Kelsey J. Brit. J. Ophthal., 1962, 46, 8, p. 449 to 467). The stimulation light-emitting diodes 114 are switched on alternately at a time interval equal to the stimulation period $T_s$ ($T_s \approx 0.7$ to 2 s). The patient 111 should smartly shift his/her gaze from one stimulation light-emitting diode to the other in step with its switching on.

The examination of the patient 111 is performed in absolute darkness, and with background illumination by the lamps 112 (usually eight two-minute cycles). With a view to finding out an initial electro-oculographic potential, the first cycle can be carried out with the "basic" (normal top) illumination. However, inasmuch as the processing procedure of the EOG signals is quite the same for the most various examination conditions (in the dark, with background illumination, basic illumination), further description will not contain the process of controlling the various types of illumination and a complete measurement process (cycle repetition every two minutes) as being not essential to the technical features of the invention.

The unit 62 incorporates also a trigger flip-flop (omitted in FIG. 7) to the mutually inverse outputs of which the stimulation light-emitting diodes 114 are connected, and an electronic stimulation switch permitting power supply to both of the light-emitting diodes 114 and remaining closed throughout the entire cycle of processing an EOG signal. The trigger flip-flop is changed over in response to a signal "62-reset" at a time interval equal to that of stimulation $T_s$, while the electronic switch is changed over against a signal "62-stimulation". Both of the signals are delivered from the output 48 of the control unit 44.

The extrema determination unit (FIG. 1) is a standard element (a digital analog to a peak detector) and is for establishing, at the output 73, the maximum value of the moduli of input codes applied to the input 67, and at the output 71, the maximum or minimum value of a signal applied to the input 67 (depending on the state of a signal delivered from the digital comparator 26 to the input 69). A change in the state of the data output 71 is accompanied with the delivery of a logic "1" signal from the output 72 to the time gate 32.

The unit 68 operates in step with a quantization frequency in response to signals delivered from the control unit 44 and applied to the input 70. Among such signals are: an extremum search gating signal "68-$f_c$", a signal "68-reset" to reset an extremum of the type opposite to the running one, a maximum modulus search permission signal "68-MAX" for the unit 75 and a signal "68-gate MAX" for remembering the modulus maximum at the output 73. There are applied to the input 69 of the unit 68 control signals of simultaneous search for a minimum and a maximum, delivered from the output 31a of the comparator 26, and type of extremum (min/max) changing-over signals delivered from the output 31b.

Whenever a signal at the output 31a is the logic "0" the unit 68 effects search for the both types (min and max) of extremum without their reset, while in the case of the logic "1" the type of extremum at the output 71 is determined by a signal from the output 31b (e.g., "0"—max, "1"—min) provided that the opposite-type extremum is searched for anew within each next first-type time interval in response to a signal "70-reset" for its zero-filling.

The unit 68 can be built on the base of, e.g., a value modulus determination circuit, a code of three circuits of code comparison with buffer registers, the digital commutator of the output 71 and logic circuits for control of register recording and reset.

The data display unit 64 delivers the measurement results from the digital discriminator 41 to indicators, or convers them into any other form of representation, as well as warns the operator of errors in detecting the presence of a stationary disturbance, unequiangular or poor gaze fixation by the patient. The unit 64 performs also the functions of normalization of the results $K_1$ of processing an EOG signal to the result $K_2$ of processing a calibrating signal from the calibrator 2:

$$U_1 = \frac{K_1}{K_2} U_2, \quad (10)$$

where
$U_1$—indicated result of processing an EOG signal;
$U_2$—reference voltage value in the calibrator unit 2;
$K_1$—resultant code of processing an EOG signal from the output the unit 41;
$K_2$—resultant code of processing a calibration signal from the output of the unit 41.

This makes it possible to render the measurement results much more stable and reliable and to avoid any drift of the parameters of the analog measuring channel (the units 5, 7, 8, 9).

The unit 64 is controlled by signals delivered by the control unit 44-"64-electrodes", "64-unequiangular fixation", 64-no gaze fixation", "64-gate" for remembering and readout of the results of processing an EOG signal, and "64-calibration" for remembering the results of processing a calibration signal for subsequent use in accordance with Eqn. (10). In addition, delivered to the input 63 of the unit 64 is a signal on the presence of a stationary disturbance, which is only to indicate the fact of detecting a stationary disturbance irrespective of the results of "sensing" the signal at the input 46 of the control unit 44, while delivered to the data input 65 is the result of automatic process of an EOG signal or of a calibration signal.

The control unit 44 represented schematically in FIG. 8, is for shaping control signals for all the units of the device and brings their operation in synchronism. As a matter of fact the unit 44 is a microprogramming control unit and, in view of minimizing the cost of hardware, the unit is built around of a microprocessor.

The control unit 44 incorporates a microprocessor 115, an interface 116 and a timer 117 interconnected by a common bus 118 for data and signal transfer. The inputs and outputs of the interface 116 are at the same time the inputs and outputs of the unit 44, except for the outputs 50 and 48 which are respectively the output of the timer 117 and a combination of the output of the timer 117 and one of the outputs of the interface 116. Using as the microprocessor 115 may be a digital switching circuit, a microprocessor with a microprogram control, a microprocessor with a hardware control, or a single-chip microprocessor. It is assumed that the unit 115 comprises also a microprocessor functional program and the required on-line memory for storing intermediate measurement results.

The unit 115 is connected, through the bus 118, to the interface 116 which shapes and accepts all external signals of the control unit 44, as well as to the timer 117 which shapes a signal having a stimulation period $T_s$ for the units 2, 62 and also for the microprocessor 115, and also a signal at a quantization frequency $f_o = 1/T_o$ which is analyzed by the microprocessor 115. The timer $T_s$ is a resettable one for providing most favourable examination conditions for the patient.

The functional algorithm of the control unit 44 are represented in FIGS. 9, 10, 10a and 10b. While considering these algorithms one can trace the operation of the whole device for processing electro-oculographic signals.

Figure 9:
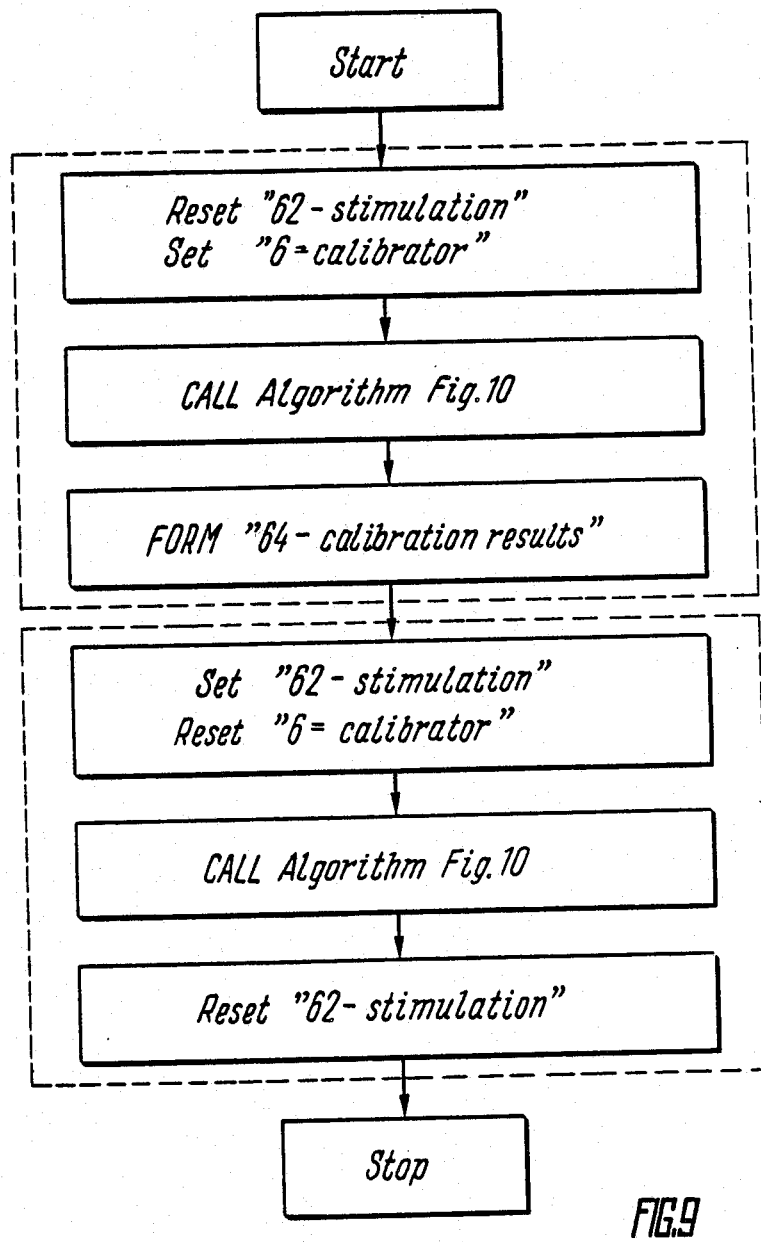
FIG. 9 is block diagram of the control unit function algorithm.

FIG. 9 illustrates a general functional algorithm of the unit 44, which consists of two stages:
 (a) processing a calibration signal from the unit 2 and remembering the calibration results in response to a signal "64-calibration". In this case the visual stimulator 62 does not operate (a signal "64-stimulator" being reset;
 (b) processing an EOG signal (a signal "6-calibrator" being reset), with the visual stimulator 62 put in operation.

Figure 10:
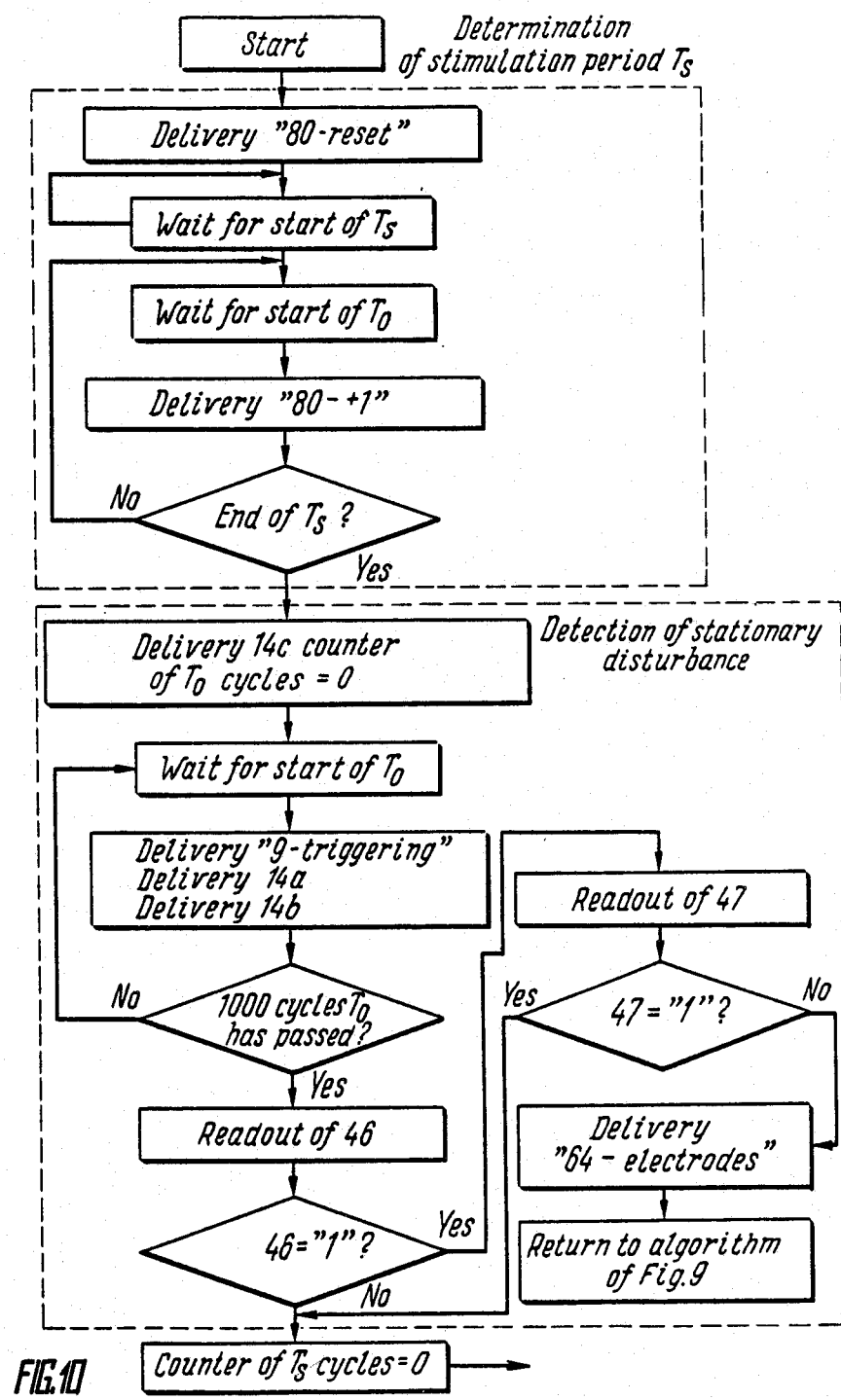
FIGS. 10, 10a and 10b are a block diagram of an alogrithm for processing electro-oculographic signals.
Figure 10A:
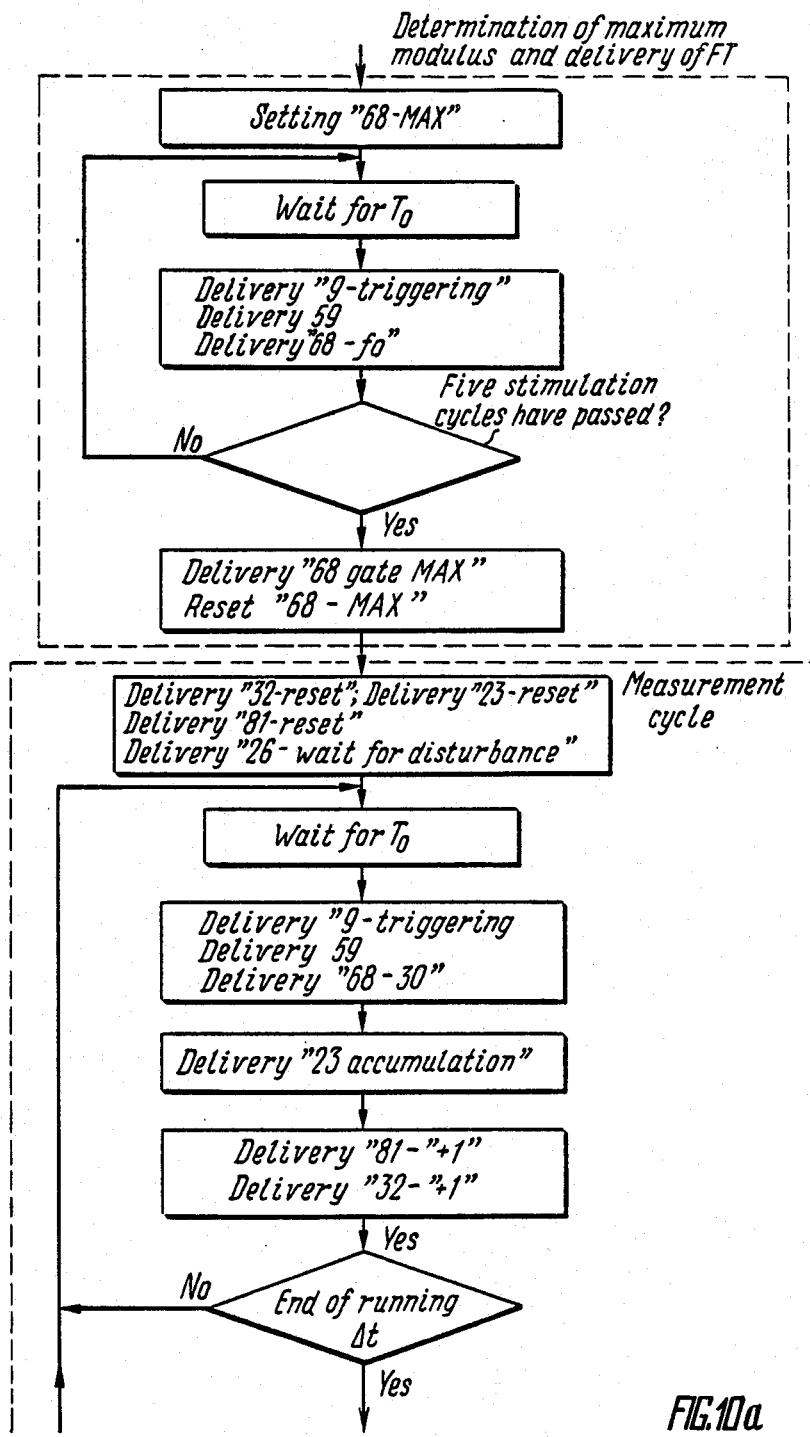
Figure 10B:
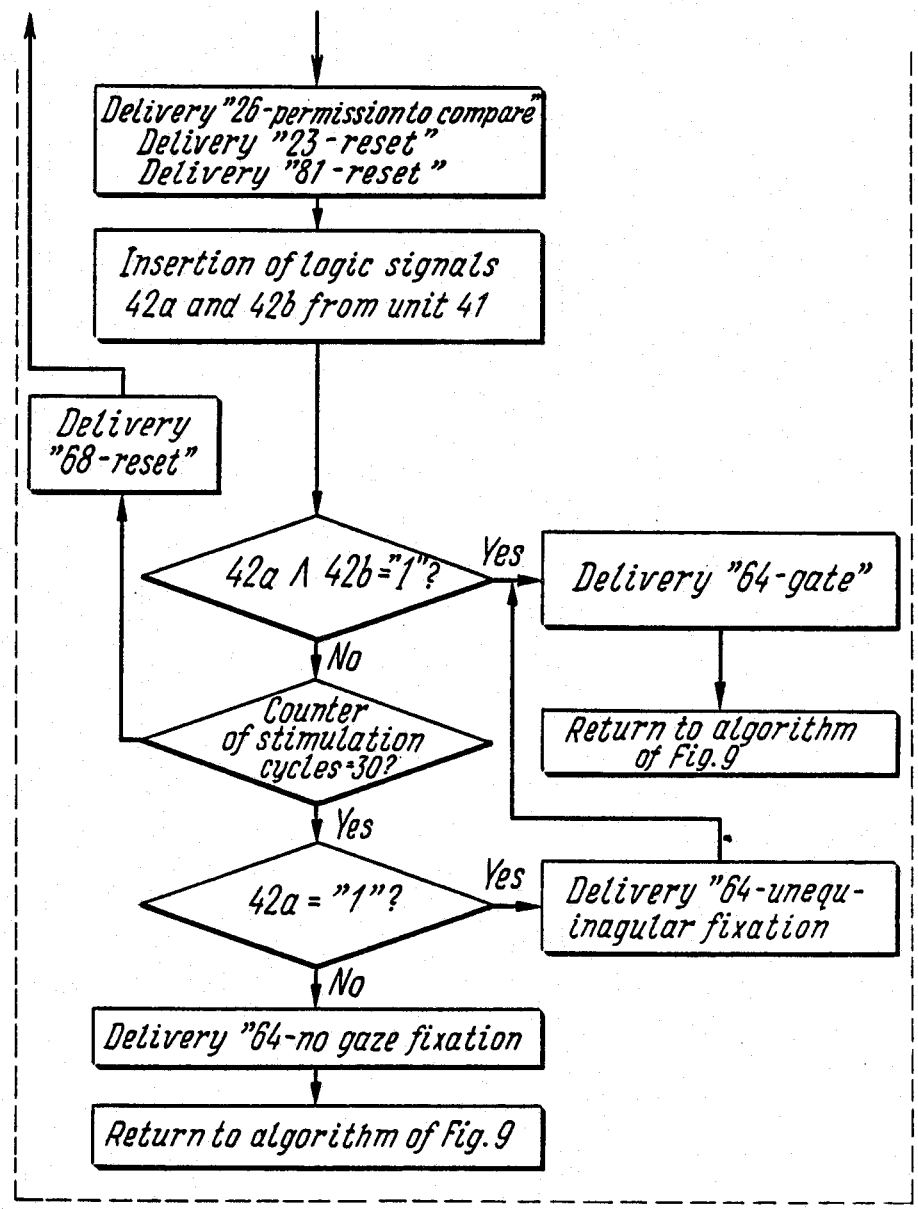

Both of the stages call the algorithm of FIGS. 10, 10a and 10b as a signal processing and measurement algorithm.

The algorithm of FIG. 9 can be employed at a subroutine level in an operating algorithm taking account of control over both "basic" and background illumination, which makes it possible to carry out a complete EOG examination consisting of a set of dark and light measurement cycles.

The principal algorithm for processing a calibration or an EOG signal is represented in FIGS. 10, 10a and 10b. The following steps in its operation can be recognized:
 (c) Determining the duration of a stimulation period;
 (d) Checking for quality application of electrodes by establishing whether a stationary disturbance is present or not;
 (e) Determining the modulus of an absolute value of a signal and shaping the functional threshold FT;
 (f) Measuring cycle.

At the step "c" after preliminary resetting the counter of the unit 80, its increment is carried out at a quantization frequency $f_o$ within a single stimulation period $T_s$.

At the step "d" there is performed accumulation (for 1000 cycles) of the moduli of amplitudes (or the squares thereof) of a stationary disturbance, delivered from the output of the digital selective filter 82 (FIG. 2) of the unit 12 to the adder 84 of the same unit, the number 1000 being assumed arbitrarily. Such accumulation is practicable for any number of quantization cycles within a period of time not shorter than a full stimulation period $T_s$. Upon reading a signal at the input 46 of the control unit 44, the presence of a stationary disturbance is judged; if so a corresponding signal is delivered to the data display unit 64 and, depending on whether a signal permitting the suppression of a stationary disturbance appears at the input 47 of the unit 44, the disturbance is suppressed, or return to the algorithm of FIG. 9 occurs.

The step "e" lasts, in a given particular case, within about four stimulation periods and consists of two substeps:
 cycles having a duration of a single first-type time interval;
 analysis cycles.

There is produced by the generator 81 within the first-type time interval having a length of $\Delta t$, a stepped linearly variable voltage in accordance with Eqn. (7) and the value Eqn. (5) is accumulated in the adder-accumulator 23. At the end of the time interval $\Delta t$ (its length being determined in the quantization cycles by $T_o$ and is shaped also by the control unit 44), transition to the analysis of the sum from the unit 23 occurs. Once the digital comparator 26 has been gated by an impulse signal "26-permission to compare" in the case of a "zero" logic signal "26-search wait", the units 32, 37, 41 operate automatically, and signals at the output 42a ("memory unit 37 filled to capacity") and at the output 42b ("end of operation") are inserted into the control unit 44. When the operation is terminated and no unequiangular fixation occurs, return to the algorithm of FIG. 9 takes place, and the results are delivered to the data display unit 64. If otherwise (that is, when the memory unit 37 is not filled to capacity, or data nonuniformity exceeds the permissible value $$\delta_A^{max}),$$

an analysis of the number of the stimulation cycles performed is carried out. In a given particular case the threshold value equals 30, since in this case (with $T_s$9 1 s) the measurement cycle can be repeated (when a signal "poor patient's eyesight" appears at the output 77 of the classification unit 78 and the patient is allowed to rest for one minute until a next cycle). One should aim at increasing the threshold number of cycles, since it makes it possible to render the detection of an intelligence EOG signal more probable.

When failure to fix patient's gaze occurs ("poor patient's eyesight", an algorithm for processing an EOG signals stops (as seen in the algorithm of FIG. 10b), and the data display unit 64 indicates an error that has occurred. Then the operator should set the selector of the unit 78, which shapes a signal "poor patient's eyesight" with the level "1" at the output 77, and should repeat the measurement cycle. However, the aforesaid process can be performed automatically against a command sent by the control signal 44 by inserting an additional 2AND gate between the output 77 of the unit 78 and the input 76 of the generator 75, as well as by establishing an additional output from the control unit 44 to the second input of the additional 2AND gate. The additional output of the unit 44 is set to "1" when poor gaze fixation is observed and all measurements can be repeated automatically beginning with the step "f" in FIG. 10. The unit 78 can also be incorporated in the control unit 44. In such a case setting the one state of signals at the inputs 16 and 76 can be carried out automatically if a corresponding error is detected.

We claim:
1. A device for processing electro-oculographic signals, comprising:
 a sensor of an electro-oculographic signal, having an output;

an amplifier-multiplexer having a first, a second and a third input and an output, said first input being connected to said sensor output;

a calibrator having an input and an output and connected through said output to said second input of the amplifier-multiplexer;

a low-pass filter having an input connected to said output of the amplifier-multiplexer, and an output;

a high-pass filter having an input connected to said output of the low-pass filter, and an output;

an analog-to-digital converter having a first input connected to said output of the high-pass filter, a second input and an output;

a stationary disturbance detection unit having a first input connected to said output of the analog-to-digital converter, a second input and an output;

a stationary disturbance suppressing unit having a first input connected to said output of the stationary disturbance detection unit, a second input connected to said output of the analog-to-digital converter, a third input, a fourth input, and an output;

a multiplier having a first input connected to said output of the stationary disturbance suppressing unit, a second input and an output;

an adder-accumulator having a first input connected to said output of the multiplier, a second input and an output;

a digital comparator having a first input connected to said output of the adder-accumulator, a second input, a third input, a first output and a second output;

a time gate having a first input connected to said first output of the digital comparator, a second input, a third input, a fourth input and an output;

a memory unit having a first input connected to said output of the time gate, a second input, a third input, and an output;

a digital discriminator having an input connected to said output of the memory unit, a first output, and a second output;

a data display unit having a first input connected to said first output of the digital discriminator, a second input connected to said output of the stationary disturbance detection unit, and a third input;

a classification unit having a first output connected to said third input of the stationary disturbance suppressing unit, and a second output;

an extrema determination unit having a first input connected to said output of the stationary disturbance suppressing unit, a second input connected to said second output of the digital comparator, a third input, a first output connected to said second input of the time gate, a second output connected to said second input of the memory unit, and a third output;

a first function generator having a first input connected to said third output of the extrema determination unit, a second input connected to said second output of the classification unit, and an output connected to said second input of the digital comparator;

a second function generator having an input and an output which is connected to said second input of the multiplier;

a stimulation period determination unit having an input and an output which is connected to said third input of the time gate;

a visual stimulator having an input;

a control unit having a first input connected to said second output of the digital discriminator, a second input connected to said second input of the data display unit, a third input connected to said first output of the classification unit, and a plurality of outputs;

said plurality of outputs of the control unit, each of them being connected to the respective said input of the visual stimulator, the third input of the amplifier-multiplexer, the input of the calibrator, the input of the second function generator, the second input of the adder-accumulator, the third input of the digital comparator, the second input of the analog-to-digital converter, the input of the stimulation period determination unit, the fourth input of the time gate, the second input of the stationary disturbance detection unit, the third input of the memory unit, the fourth input of the stationary disturbance suppressing unit, the third input of the data display unit, and the third input of the extrema determination unit.

* * * * *